United States Patent

Oumar-Mahamat et al.

Patent Number: 5,514,289
Date of Patent: May 7, 1996

[54] DIHYDROBENZOTHIOPHENES AS ANTIOXIDANT AND ANTIWEAR ADDITIVES

[75] Inventors: Halou Oumar-Mahamat, Plainsboro; Andrew G. Horodysky, Cherry Hill; Andrew Jeng, Paulsboro, all of N.J.

[73] Assignee: Mobil Oil Corporation, Fairfax, Va.

[21] Appl. No.: 421,103

[22] Filed: Apr. 13, 1995

[51] Int. Cl.$^6$ .................... C10M 135/34; C10L 1/24
[52] U.S. Cl. .................... 252/45; 252/47; 252/48.2; 44/350; 44/352; 549/49; 549/83
[58] Field of Search .................... 549/49, 83; 44/350, 44/352; 252/45

[56] References Cited

U.S. PATENT DOCUMENTS

| | | | |
|---|---|---|---|
| 2,686,185 | 8/1954 | Kreuz | 549/49 |
| 3,070,606 | 12/1962 | Anderson | 549/49 |
| 3,910,955 | 10/1975 | Chapman et al. | 549/49 |
| 4,124,514 | 11/1978 | Yaffe | 252/45 |
| 4,143,052 | 3/1979 | Barrault et al. | 549/49 |
| 4,280,894 | 7/1981 | Taylor | 208/15 |
| 4,626,368 | 12/1986 | Cardis | 252/49.9 |
| 4,737,301 | 4/1988 | Bloch et al. | 252/45 |
| 5,288,418 | 2/1994 | Farng et al. | 252/49.9 |
| 5,292,894 | 3/1994 | Ebel et al. | 549/49 |
| 5,342,532 | 8/1994 | Takei et al. | 252/45 |
| 5,372,734 | 12/1994 | Law et al. | 549/49 |

*Primary Examiner*—Ellen M. McAvoy
*Attorney, Agent, or Firm*—Alexander J. McKillop; Malcolm D. Keen; Charles A. Malone

[57] ABSTRACT

Novel dihydrobenzothiophenes prepared via condensation of arylthiols and carbonyl or epoxide containing reagents have been found to be effective antioxidant and antiwear additives in lubricant applications. These additives are made from relatively low cost mercaptans and carbonyl compounds in a one-step high yield reaction.

28 Claims, No Drawings

DIHYDROBENZOTHIOPHENES AS ANTIOXIDANT AND ANTIWEAR ADDITIVES

FIELD OF THE INVENTION

This invention is directed to dihydrobenzothiophenes prepared via condensation of arylthiols and carbonyl or epoxide containing or generating reagents which are useful as multifunctional antioxidation, antiwear, and anticorrosion lubricant additives. It also concerns a process for making said additives as well as to lubricant compositions comprised thereof.

BACKGROUND OF THE INVENTION

The use of hindered phenols, such as 2,6-di-tert-butylphenol and 2,6-di-tert-butyl-para-cresol, has been well known for their thermal/oxidation stabilizing properties in a variety of lubricant, polymer and elastomer applications.

Benzotriazole or a substituted benzotriazole compound reacted with an alkyl aldehyde and dialkylhydrogen phosphites provide products which improve the load-carrying, antiwear properties of lubricant oils and greases. These reactants are disclosed in U.S. Pat. No. 4,626,368 which issued to Cardis on Dec. 2, 1986. Amine coupled condensation products of hindered phenols and phosphites are disclosed in U.S. Pat. No. 5,288,418 which issued to Farng et al. on Feb. 22, 1994. These products were found to be effective antioxidant/antiwear additives for lubricants. These patents are incorporated by reference herein.

Although commercially available hindered phenol and aromatic amine antioxidants provide excellent oxidation protection, it is desirable to have compounds which can provide for even greater oxidation protection while providing for additional antiwear properties as well as other multifunctional properties.

Therefore, what is needed is a novel lubricant additive compound with exceptional antioxidant activity combined with additional antiwear properties as well as other beneficial multifunctional properties for incorporation into improved lubricant compositions.

SUMMARY OF THE INVENTION

It has been found that lubricant and fuel compositions containing a small additive concentration of a novel reaction product of an arylthiol and carbonyl or epoxide provide exceptional oxidative stability and possess excellent antiwear properties coupled with good extreme pressure activities. Additional cleanliness, high temperature stability, extreme pressure, metal deactivation, friction reducing, and corrosion inhibition properties are also expected with many of the disclosed compositions of the instant invention.

Resultant cyclic additive compounds provide exceptional oxidative stability, presumably due to their labile benzylic hydrogens acting as chain breaking antioxidants. An additional peroxide decomposing antioxidant property is provided by the presence of sulfur. Sulfur also contributes to the antiwear properties of the lubricant formulations treated with these novel additives. In addition to lubricant applications, these novel compositions may be used in hydrocarbon, alcoholic, or mixed hydrocarbon/oxygenated fuels to impart similar performance characteristics thereto. Furthermore, these novel compounds may be used as a minor component in a mixture of lubricants or even as a major synlube when combined with appropriate substituents.

Products containing additives resultant from these compositions display good stability and compatibility when used in the presence of other commonly used additives in fuel or lubricant compositions.

Accordingly, this invention is directed to lubricant compositions comprising a major amount of an oil of lubricating viscosity and a minor multifunctional amount of the herein described novel arylthiol and carbonyl or epoxide composition.

It is therefore an object of this invention to provide for improved lubricant compositions comprising the aforementioned multifunctional additive reaction products.

BRIEF DESCRIPTION OF THE PREFERRED EMBODIMENTS

This invention describes novel antioxidants and a facile process of making them. These new cyclic sulfides provide exceptional oxidation protection when used in lubricants, thereby exceeding the antioxidant activity of commercially obtained hindered phenol and aromatic amine antioxidants. Also, the presence of sulfur confers an additional antiwear property. Additional cleanliness, high temperature stability, extreme pressure, friction reducing, metal deactivation and corrosion inhibition characteristics are also expected.

In one preferred embodiment of this invention, dihydrobenzothiophenes are made from reactions of arylthiols with epoxides. Another preferred embodiment of this invention is directed to dihydroisobenzothiophenes obtained from reactions of benzylmercaptans and aldehydes. Both of these embodiments provide for novel antioxidant and antiwear additives resultant from the reaction products.

When carrying out one embodiment of the practice of this invention, aliphatic or aromatic epoxides are reacted with arylthiols in a one step reaction to yield dihydrobenzothiophene derivatives as generally described below:

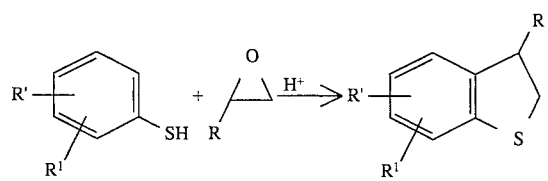

where R is hydrogen, a $C_1$ to $C_{100}$ hydrocarbyl and more preferably, $C_1$ to $C_{40}$ hydrocarbyl selected from the group consisting of alkyl, alkenyl, alkaryl, arylalkyl, aryl, cycloalkenyl, or cycloalkyl which optionally contains a heteroatom selected from a member of the group consisting of sulfur, oxygen or nitrogen; and $R^1$ is hydrogen, a $C_1$ to $C_{60}$ hydrocarbyl selected from the group consisting of alkyl, alkenyl, alkaryl, arylalkyl, aryl, cycloalkenyl, or cycloalkyl that optionally contains a member selected from the group consisting of sulfur, oxygen or nitrogen.

When conducting another embodiment of the practice of this invention, aliphatic or aromatic aldehydes are reacted in a similar manner with benzylmercaptans to yield dihydroisobenzothiophene derivatives:

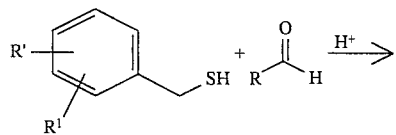

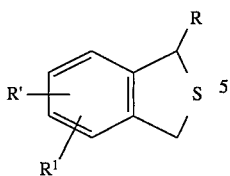

where R is hydrogen, a $C_1$ to $C_{100}$ hydrocarbyl and more preferably, $C_1$ to $C_{40}$ hydrocarbyl selected from the group consisting of alkyl, alkenyl, alkaryl, arylalkyl, aryl, cycloalkenyl, or cycloalkyl which optionally contains a heteroatom selected from a member of the group consisting of sulfur, oxygen or nitrogen; and $R^1$ is hydrogen, a $C_1$ to $C_{60}$ hydrocarbyl selected from the group consisting of alkyl, alkenyl, alkaryl, arylalkyl, aryl, cycloalkenyl, or cycloalkyl that optionally contains a member selected from the group consisting of sulfur, oxygen or nitrogen.

In the practice of this invention, equimolar quantities, temperatures between about 120° C. to about 160° C., and reaction times of about 14 to about 24 hours are generally preferred. However, an excess of either reactant can be used. In order to enhance the reaction, concentrated sulfuric acid or an alternate analogous mineral acid such as hydrochloric or hydroflouric acid can be utilized as a reaction catalyst.

Generally speaking, conditions for the above described reactions may vary widely depending upon specific reactants, the presence or absence of a solvent and the like. Any suitable set of reaction conditions known to the art may be used. Generally, stoichiometric quantities of reactants are used. However, equimolar, more than molar or less than molar amounts may be used. An excess of up to 100% or more of any of the reactants can be used. Preferably, the molar ratio of reactants varies from about 10:10:0.05 moles to about 1:1:0.005 moles respectively of arylthiol, aliphatic or aromatic expoxides or aldehydes, and sulfuric acid. The reaction temperature may vary from ambient to about 250° C. or reflux, the pressure may vary from ambient or autogenous to about 1,000 psi.

Suitable aliphatic or aromatic aldehydes and mixtures thereof which can be used herein include but are not limited to the following; butyraldehyde, 2-ethyhexanal, formaldehyde, para-tolualdehyde, para-ethylbenzaldehyde, salicylaldehyde, and compounds similar thereto. Paraformaldehyde is a preferred carbonyl generating species. Of these, para-tolualdehyde, para-ethylbenzaldehyde, and salicylaldehyde are preferred.

Any suitable hydrocarbon solvent such as toluene, hexane or a xylene may be used if desired.

The additives embodied herein are utilized in lubricating oil or grease compositions in an amount which imparts significant antiwear characteristics to the oil or grease as well as reducing the friction of engines operating with the oil in its crankcase. Concentrations of about 0.001 to about 10 wt % based on the total weight of the composition can be used. Preferably, the concentration is from 0.1 to about 3 wt. %.

The additives have the ability to improve the above noted characteristics of various oleaginous materials such as hydrocarbyl lubricating media which may comprise liquid oils in the form of either a mineral oil or a synthetic oil, or mixtures of synthetic and mineral oil, or in the form of a grease in which the aforementioned oils are employed as a vehicle.

In general, mineral oils, both paraffinic, naphthenic and mixtures thereof, employed as the lubricant, or grease vehicle, may be of any suitable lubricating viscosity range, as for example, from about 45 SUS at 100° F. to about 6,000 SUS at 100° F. and preferably, from about 50° to about 250 SUS at 210° F. These oils may have viscosity indexes preferably ranging to about 95. The average molecular weights of these oils may range from about 250 to about 800. Where the lubricant is to be employed in the form of a grease, the lubricating oil is generally employed in an amount sufficient to balance the total grease composition, after accounting for the desired quantity of the thickening agent, and other additive components to be included in the grease formulation.

A wide variety of materials may be employed as thickening or gelling agents. These may include any of the conventional metal salts or soaps, which are dispersed in the lubricating vehicle in grease-forming quantities in an amount sufficient to impart to the resulting grease composition the desired consistency. Other thickening agents that may be employed in the grease formulation may comprise the non-soap thickeners, such as surface-modified clays and silicas, aryl ureas, calcium complexes and similar materials. In general, grease thickeners may be employed which do not melt and dissolve when used at the required temperature within a particular environment; however, in all other respects, any material which is normally employed for thickening or gelling hydrocarbon fluids for forming grease can be used in preparing grease in accordance with the present invention.

In instances where synthetic oils, or synthetic oils employed as the lubricant or vehicle for the grease, are desired in preference to mineral oils, or in combination therewith, various compounds of this type may be successfully utilized. Typical synthetic oils include, but are not limited to, polyisobutylene, polybutenes, hydrogenated polydecenes, polypropylene glycol, polyethylene glycol, trimethylpropane esters, neopentyl and pentaerythritol esters, di(2-ethylhexyl) sebacate, di(2-ethylhexyl) adipate, dibutyl phthalate, fluorocarbons, silicate esters, silanes, esters of phosphorus-containing acids, liquid ureas, ferrocene derivatives, hydrogenated synthetic oils, chain-type polyphenyls, siloxanes and silicones (polysiloxanes), alkyl-substituted diphenyl ethers typified by a butyl-substituted bis(p-phenoxy phenyl) ether, and phenoxy phenylethers.

It is to be understood, however, that the compositions contemplated herein can also contain other materials. For example, corrosion inhibitors, extreme pressure agents, low temperature properties modifiers and the like can be used as exemplified respectively by metallic phenates or sulfonates, polymeric succinimides, non-metallic or metallic phosphorodithioates and the like. These materials do not detract from the value of the compositions of this invention, rather the materials serve to impart their customary properties to the particular compositions in which they are incorporated.

The additives in accordance with the invention are believed to be highly useful in fuel compositions, particularly in liquid hydrocarbon fuels or oxygenated fuels such as alcoholic fuels, ether containing fuels or the like and mixtures thereof. Included among these fuels are gasohols, fuels containing alcohols such as methanol, ether or ethers such as t-butyl methyl ether. The present additives are used in fuel compositions in amounts ranging from about 1 to about 1,000 pounds of additive per 1,000 barrels of fuel and preferably from about 10 to about 250 pounds per 1,000 pounds of fuel. In addition to liquid hydrocarbon and oxygenated combustion fuels, distillate fuels and fuel oils are also contemplated. Other additives such as detergents, inhibitors, antirusts, and octane improvers can also be used with the compounds of this invention.

The following examples are merely illustrative and are not meant to be limitations.

EXAMPLE 1

Approximately 55 grams (0.5 mols) of thiophenol and 183 grams (0.5 mols) of polyisobutylene oxide ("ACTIPOL E6" commercially obtained from Amoco Chemical Co.) was placed in 200 mls of toluene. In the presence of 0.25 grams (2.5 millimoles) of concentrated sulfuric acid, the reactants were heated at reflux temperature (130° C.) for 24 hours under an inert atmosphere. Water formed during the reaction was constantly removed by azeotropic distillation using a moisture trap i.e., a Dean-Stark apparatus. Solvent was then stripped via distillation by raising the temperature to 160° C. Light ends of the remaining residue were removed under vacuum to yield 208 grams of yellow liquid.

EXAMPLE 2

Approximately 55 grams (0.5 mols) of thiophenol and 183 grams (0.5 mols) of polyisobutylene oxide ("ACTIPOL E6" commercially obtained from Amoco Chemical Co.), and 0.25 grams (2.5 millimoles) of concentrated sulfuric acid were heated at 125° C. for 20 hours under an inert atmosphere. The unreacted components were removed under vacuum to yield 194 grams of yellow liquid.

EXAMPLE 3

The reaction was run similarly to Example 1 using benzylmercaptan in place of thiophenol and 2-ethylhexanal in place of polyisobutylene oxide.

EXAMPLE 4

The reaction was run similarly to Example 2 using benzylmercaptan in place of thiophenol and 2-ethylhexanal in place of polyisobutylene oxide.

EXAMPLE 5

The reaction was run similarly to Example 1 using 1 mole of thiophenol and 1 mole of styrene oxide in place of 0.5 mole of polyisobutylene oxide. In addition, styrene oxide was added in small portions to limit the heat of the exothermic reaction.

The antioxidant properties of the examples were evaluated using the Catalytic Oxidation Test at both 325° F. for 40 hours and 72 hours. The results displayed on the following Tables 1 and 2 show exceptionally good control of oxidation as measured by change in acidity and viscosity increase. The products of the Examples were compared to high quality hindered phenol and aryl amine antioxidants and found to be significantly superior to these two types of commercial antioxidants.

The Catalytic Oxidation Test consists basically of bubbling a stream of air through a volume of the lubricant at the rate of five liters per hour respectively at 325° F. for 40 hours and 72 hours. See U.S. Pat. No. 3,682,980 incorporated herein by reference for further details.

TABLE 1

Catalytic Oxidation Test
40 Hours, 325° F.

| Item | Additive Conc. (wt %) | Change in Acid Number $\Delta$TAN | Percent Change in Viscosity $\Delta$KV % |
|---|---|---|---|
| Base oil (200 second, solvent refined, paraffinic neutral, mineral oil) | — | 13.60 | 338.89 |
| Example 1 in above base oil | 1 | 3.42 | 27.00 |
| Example 2 in above base oil | 1 | 1.06 | 7.12 |
| Example 3 in above base oil | 1 | 2.74 | 21.25 |
| Example 4 in above base oil | 1 | 2.79 | 22.45 |
| "ETHYL 702", commercial hindered phenolic antioxidant | 1 | 9.80 | 72.34 |
| "IRGANOX L57", commercial alkylated diphenylamine antioxidant | 1 | 4.30 | 24.05 |

TABLE 2

Catalytic Oxidation Test
72 Hours, 325° F.

| Item | Additive Conc. (wt %) | Change in Acid Number $\Delta$TAN | Percent Change in Viscosity $\Delta$KV % |
|---|---|---|---|
| Base oil (200 second, solvent refined, paraffinic neutral, mineral oil) | — | 24.06 | 2,942.60 |
| Example 1 in above base oil | 1 | 4.40 | 35.01 |
| Example 2 in above base oil | 1 | 3.44 | 29.51 |

TABLE 2-continued

Catalytic Oxidation Test
72 Hours, 325° F.

| Item | Additive Conc. (wt %) | Change in Acid Number ΔTAN | Percent Change in Viscosity ΔKV % |
|---|---|---|---|
| Example 3 in above base oil | 1 | 4.38 | 31.85 |
| Example 4 in above base oil | 1 | 6.26 | 47.69 |
| "ETHYL 702", commercial hindered phenolic antioxidant | 1 | 18.92 | 635.12 |
| "IRGANOX L57", commercial alkylated diphenylamine antioxidant | 1 | 14.70 | 121.40 |

As shown above, the products of this invention show considerable antioxidant activity as evidenced by the control of viscosity and acidity increase even when compared to very active commercial antioxidants.

The product of the above Examples was also blended into fully formulated middle distillate base oil and evaluated for antiwear performance using the Four-Ball test (ASTM Method D-2266) as shown in Table 3 below. See also U.S. Pat. No. 4,761,482 for further details. This patent is incorporated herein by reference.

The antiwear properties of the Examples were measured using the 4-Ball Wear Test. The results show the antiwear property improvement as measured by Wear Scar Diameter and K Factor (a dimensionless wear coefficient proportional to the wear volume of metal lost).

* Wear Coefficient K

Dimensionless K is defined as $$K = \frac{VH}{dW} \text{ where}$$

where

V=volume, $mm^3$

H=hardness (725 $kg/mm^2$ for 52100 steel)

d=(23.3 mm/rev) (RPM× time)

W=(0.408) (Load in kg)

The wear volume V will be calculated from the wear scar diameter D in mm as follows:

$$V = [15.5\ D^3 - 0.0103L]D \times 10^{-3} mm^3$$

where L is the machine load in kg. This equation considers the elastic deformation of the steel balls. For 60 kg load, the equation is $$V = [15.5\ D^3 - 0.618]D \times 10^{-3} mm^3$$

TABLE 3

FOUR BALL WEAR TEST RESULTS
75° C. @ 1,800 rpm, 30 min., 40 kg

| Item | Additive Conc. (wt %) | Wear Scar Diameter (mm) | K Factor 10-8 |
|---|---|---|---|
| Base oil (80/20 mixture of solvent paraffinic bright and solvent paraffinic neutral, mineral oils) | — | 0.627 | 7.25 |
| Example 3 in above base oil | 1 | 0.506 | 2.8 |
| Example 4 in above base oil | 1 | 0.475 | 2.1 |

TABLE 3-continued

FOUR BALL WEAR TEST RESULTS
75° C. @ 1,800 rpm, 30 min., 40 kg

| Item | Additive Conc. (wt %) | Wear Scar Diameter (mm) | K Factor 10-8 |
|---|---|---|---|
| Example 5 in above base oil | 1 | 0.550 | 4.2 |

INTERPRETATION OF TEST RESULTS

As shown above, the products of this invention demonstrate considerable antiwear (AW) activity as evidenced by the improvement of the wear scar diameter and the k factor. Additionally, as above mentioned, the products of this invention show considerable antioxidant activity as evidenced by the control of viscosity and acidity increase.

Although these products have demonstrated significant antiwear activity, they are extremely non-corrosive to metals, such as copper alloys.

The use of additive concentrations of this invention in fuels will significantly reduce fuel pump and injector components wear problems associated with low sulfur and aromatics containing fuels. They will also improve the combustion properties of these fuels and as such reduce particulate emissions. These additives potentially may benefit fuel and lubricant properties by reducing hydrocarbon, carbon monoxide, and NOx emissions, and by improving antiwear and fuel economy characteristics and extending engine life.

Although the present invention has been described with preferred embodiments, it is to be understood that modifications and variations may be resorted to, without departing from the spirit and scope of this invention, as those skilled in the art will readily understand. Such variations and modifications are considered to be within the purview and scope of the appended claims.

What is claimed:

1. An improved lubricant composition comprising a major proportion of an oil of lubricating viscosity or grease prepared therefrom or an improved fuel composition comprising a major proportion of a liquid hydrocarbon or oxygenated fuel or mixtures thereof and a minor amount of a multifunctional high temperature, antiwear, antioxidant, anticorrosion additive product of reaction prepared by reacting an arylthiol with (a) an aliphatic or an aromatic epoxide or (b) an aromatic or aliphatic aldehyde thereby forming a dihydrobenzothiophene additive condensation product wherein the reaction is carried out at temperatures varying from ambient to about 250° C. under ambient pressure up to 1,000 psi or autogenous pressures for a time sufficient to obtain the desired dihydrobenzothiophene additive product of reaction and wherein the reaction is carried out in molar ratios of reactants varying from equimolar to more than molar to less than molar.

2. The composition of claim 1 wherein said dihydrobenzothiophene additive product is prepared in a single-step batch or single-step continuous process wherein the reaction is represented by the following equation:

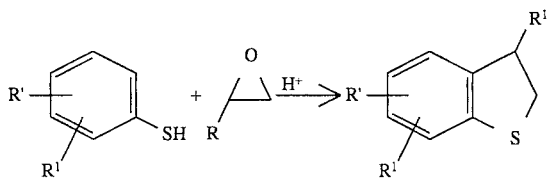

where R is hydrogen, a $C_1$ to $C_{100}$ hydrocarbyl selected from the group consisting of alkyl, alkenyl, alkaryl, arylalkyl, aryl, cycloalkenyl, or cycloalkyl which optionally contains a heteroatom selected from a member of the group consisting of sulfur, oxygen or nitrogen; and $R^1$ is hydrogen, a $C_1$ to $C_{60}$ hydrocarbyl selected from the group consisting of alkyl, alkenyl, alkaryl, arylalkyl, aryl, cycloalkenyl, or cycloalkyl that optionally contains a member selected from the group consisting of sulfur, oxygen or nitrogen.

3. The composition of claim 1 wherein said dihydrobenzothiophene additive product is prepared in a single-step batch or single-step continuous process wherein the reaction is represented by the following equation:

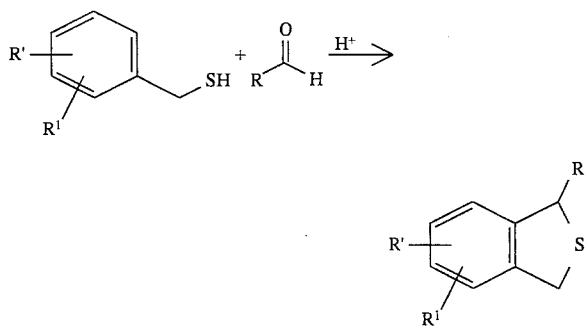

where R is hydrogen, a $C_1$ to $C_{100}$ hydrocarbyl selected from the group consisting of alkyl, alkenyl, alkaryl, arylalkyl, aryl, cycloalkenyl, or cycloalkyl which optionally contains a heteroatom selected from a member of the group consisting of sulfur, oxygen or nitrogen; and $R^1$ is hydrogen, a $C_1$ to $C_{60}$ hydrocarbyl selected from the group consisting of alkyl, alkenyl, alkaryl, arylalkyl, aryl, cycloalkenyl, or cycloalkyl that optionally contains a member selected from the group consisting of sulfur, oxygen or nitrogen.

4. The composition of claim 1 wherein said dihydrobenzothiophene additive product has the following structure:

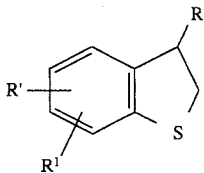

where R is hydrogen, a $C_1$ to $C_{100}$ hydrocarbyl selected from the group consisting of alkyl, alkenyl, alkaryl, arylalkyl, aryl, cycloalkenyl, or cycloalkyl which optionally contains a heteroatom selected from a member of the group consisting of sulfur, oxygen or nitrogen; and $R^1$ is hydrogen, a $C_1$ to $C_{60}$ hydrocarbyl selected from the group consisting of alkyl, alkenyl, alkaryl, arylalkyl, aryl, cycloalkenyl, or cycloalkyl that optionally contains a member selected from the group consisting of sulfur, oxygen or nitrogen.

5. The composition of claim 1 wherein the reactants are thiophenol, polyisobutylene oxide, and a mineral acid catalyst.

6. The composition of claim 1 wherein the reactants are benzylmercaptan, 2-ethylhexanal, and a mineral acid catalyst.

7. The composition of claim 1 wherein the reactants are thiophenol, styrene oxide, and a mineral acid catalyst.

8. The composition of claim 1 where a mineral acid catalyst is utilized.

9. The composition of claim 1 where sulfuric acid is used as a catalyst.

10. The composition of claim 1 wherein the lubricant is an oil of lubricating viscosity selected from the group consisting of (1) mineral oils, (2) synthetic oils, (3) or mixtures of mineral and synthetic oils or is (4) a grease prepared from any one of (1) , (2) or (3).

11. The composition of claim 1 wherein the lubricant contains from about 0.001 to about 10 wt % based on the total weight of the composition of the additive product of reaction.

12. The composition of claim 10 wherein the lubricant is a mineral oil.

13. A process of preparing a multifunctional high temperature, antioxidant, antiwear, anticorrosion additive product prepared by reacting an arylthiol with (a) an aliphatic or an aromatic epoxide or (b) an aromatic or aliphatic aldehyde thereby forming a dihydrobenzothiophene additive condensation product wherein the reaction is carried out at temperatures varying from ambient to about 250° C. under ambient pressure up to 1,000 psi or autogenous pressures for a time sufficient to obtain the desired dihydrobenzothiophene additive product of reaction and wherein the reaction is carried out in molar ratios of reactants varying from equimolar to more than molar to less than molar.

14. The process as recited in claim 13 wherein said dihydrobenzothiophene additive product is prepared in a single-step batch or single-step continuous process wherein the reaction is represented by the following equation:

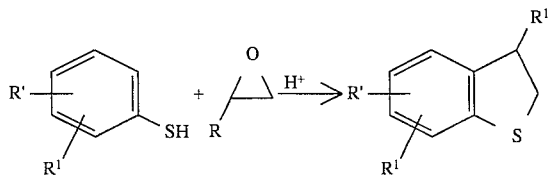

where R is hydrogen, a $C_1$ to $C_{100}$ hydrocarbyl selected from the group consisting of alkyl, alkenyl, alkaryl, arylalkyl, aryl, cycloalkenyl, or cycloalkyl which optionally contains a heteroatom selected from a member of the group consisting of sulfur, oxygen or nitrogen; and $R^1$ is hydrogen, a $C_1$ to $C_{60}$ hydrocarbyl selected from the group consisting of alkyl, alkenyl, alkaryl, arylalkyl, aryl, cycloalkenyl, or cycloalkyl that optionally contains a member selected from the group consisting of sulfur, oxygen or nitrogen.

15. The process as recited in claim 13 wherein said dihydrobenzothiophene additive product is prepared in a single-step batch or single-step continuous process wherein the reaction is represented by the following equation:

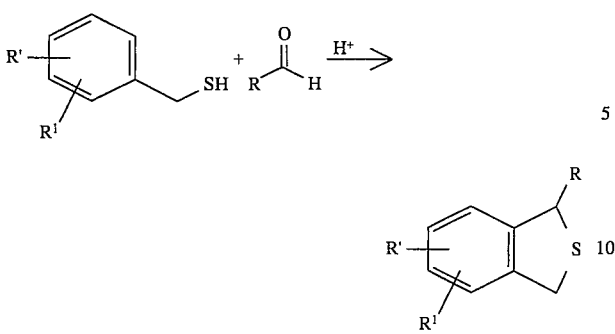

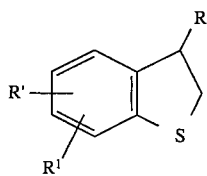

where R is hydrogen, a $C_1$ to $C_{100}$ hydrocarbyl selected from the group consisting of alkyl, alkenyl, alkaryl, arylalkyl, aryl, cycloalkenyl, or cycloalkyl which optionally contains a heteroatom selected from a member of the group consisting of sulfur, oxygen or nitrogen; and $R^1$ is hydrogen, a $C_1$ to $C_{60}$ hydrocarbyl selected from the group consisting of alkyl, alkenyl, alkaryl, arylalkyl, aryl, cycloalkenyl, or cycloalkyl that optionally contains a member selected from the group consisting of sulfur, oxygen or nitrogen.

16. The process as recited in claim 13 wherein said dihydrobenzothiophene additive product has the following structure:

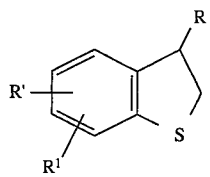

where R is hydrogen, a $C_1$ to $C_{100}$ hydrocarbyl selected from the group consisting of alkyl, alkenyl, alkaryl, arylalkyl, aryl, cycloalkenyl, or cycloalkyl which optionally contains a heteroatom selected from a member of the group consisting of sulfur, oxygen or nitrogen; and $R^1$ is hydrogen, a $C_1$ to $C_{60}$ hydrocarbyl selected from the group consisting of alkyl, alkenyl, alkaryl, arylalkyl, aryl, cycloalkenyl, or cycloalkyl that optionally contains a member selected from the group consisting of sulfur, oxygen or nitrogen.

17. The process as recited in claim 13 wherein the reactants are thiophenol and a member selected from the group consisting of polyisobutylene oxide or styrene oxide in combination with a sulfuric acid catalyst which reaction occurs under ambient pressure, a temperature of about 120° C. to about 160° C. for about 20 to about 24 hours.

18. The process as recited in claim 13 wherein the reactants are benzylmercaptan and 2-ethylhexanal in combination with a sulfuric acid catalyst which reaction occurs under ambient pressure, a temperature of about 120° C. to about 160° C. for about 20 to about 24 hours.

19. The process as recited in claim 13 where a sulfuric acid catalyst is utilized.

20. A multifunctional high temperature, antioxidant, antiwear, anticorrosion lubricant additive product of reaction prepared by reacting an arylthiol with (a) an aliphatic or an aromatic epoxide or (b) an aromatic or aliphatic aldehyde thereby forming a dihydrobenzothiophene additive condensation product wherein the reaction is carried out at temperatures varying from ambient to about 250° C. under ambient pressure up to 1,000 psi or autogenous pressures for a time sufficient to obtain the desired dihydrobenzothiophene additive product of reaction and wherein the reaction is carried out in molar ratios of reactants varying from equimolar to more than molar to less than molar.

21. The additive product of reaction as recited in claim 20 wherein said dihydrobenzothiophene additive product has the following structure:

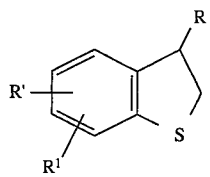

where R is hydrogen, a $C_1$ to $C_{100}$ hydrocarbyl selected from the group consisting of alkyl, alkenyl, alkaryl, arylalkyl, aryl, cycloalkenyl, or cycloalkyl which optionally contains a heteroatom selected from a member of the group consisting of sulfur, oxygen or nitrogen; and $R^1$ is hydrogen, a $C_1$ to $C_{60}$ hydrocarbyl selected from the group consisting of alkyl, alkenyl, alkaryl, arylalkyl, aryl, cycloalkenyl, or cycloalkyl that optionally contains a member selected from the group consisting of sulfur, oxygen or nitrogen.

22. The additive reaction product as recited in claim 20 where a sulfuric acid catalyst is utilized.

23. The composition of claim 1 wherein the fuel is selected from the group consisting of gasolines, alcoholic fuels, other oxygenated fuels or mixtures thereof and distillate fuels.

24. The composition of claim 23 wherein the fuel contains from about 1 to about 1,000 pounds, based on the total weight of the composition, of the additive product of reaction.

25. A multifunctional high temperature, antioxidant, antiwear, anticorrosion lubricant additive product of reaction prepared by reacting an arylthiol with (a) an aliphatic or an aromatic epoxide or (b) an aromatic or aliphatic aldehyde wherein the reaction is carried out at temperatures varying from ambient to about 250° C. under ambient pressure up to 1,000 psi or autogenous pressures for a time sufficient to obtain the desired dihydrobenzothiophene additive product of reaction and wherein the reaction is carried out in molar ratios of reactants varying from equimolar to more than molar to less than molar.

26. The additive reaction product as recited in claim 25 where a sulfuric acid catalyst is utilized.

27. The additive reaction product as recited in claim 25 where a mineral acid catalyst is utilized which is selected from a member of the group consisting of sulfuric acid, hydrochloric acid, or hydroflouric acid.

28. A method for improving the high temperature, antiwear, antioxidant, and anticorrosion properties of a major amount of oil of lubricating viscosity or grease prepared therefrom or a fuel composition comprising a major amount of a liquid hydrocarbon or oxygenated fuel or mixtures thereof comprising adding to said oil, grease, or fuel a minor amount of an additive product of reaction prepared by reacting a $C_1$ to $C_{200}$ arylthiol with (a) an aliphatic or an aromatic epoxide or (b) an aromatic or aliphatic aldehyde thereby forming a dihydrobenzothiophene additive condensation product wherein the reaction is carried out at temperatures varying from ambient to about 250° C. under ambient pressure up to 1,000 psi or autogenous pressures for a time sufficient to obtain the desired dihydrobenzothiophene additive product of reaction and wherein the reaction is carried out in molar ratios of reactants varying from equimolar to more than molar to less than molar.

* * * * *